(12) United States Patent
Hashimoto et al.

(10) Patent No.: US 8,519,998 B2
(45) Date of Patent: Aug. 27, 2013

(54) ULTRASONIC IMAGING APPARATUS

(75) Inventors: Shinichi Hashimoto, Otawara (JP);
Itsuki Kuga, Nasushiobara (JP); Eiichi Shiki, Otawara (JP)

(73) Assignees: Kabushiki Kaisha Toshiba, Tokyo (JP);
Toshiba Medical Systems Corporation, Otawara-shi (JP)

( * ) Notice: Subject to any disclaimer, the term of this patent is extended or adjusted under 35 U.S.C. 154(b) by 656 days.

(21) Appl. No.: 12/170,021

(22) Filed: Jul. 9, 2008

(65) Prior Publication Data

US 2009/0015587 A1    Jan. 15, 2009

(30) Foreign Application Priority Data

Jul. 9, 2007  (JP) ................................. 2007-179788

(51) Int. Cl.
*G06T 15/08* (2011.01)
*G09G 5/02* (2006.01)
*A61B 8/06* (2006.01)

(52) U.S. Cl.
USPC ............................ 345/424; 345/589; 600/453

(58) Field of Classification Search
USPC ................................................. 600/407–480
See application file for complete search history.

(56) References Cited

U.S. PATENT DOCUMENTS

| | | | | |
|---|---|---|---|---|
| 5,479,926 A | * | 1/1996 | Ustuner et al. ............... | 600/440 |
| 6,068,598 A | * | 5/2000 | Pan et al. ..................... | 600/453 |
| 6,658,080 B1 | * | 12/2003 | Poole et al. ................... | 378/4 |
| 2003/0097068 A1 | * | 5/2003 | Hossack et al. ............... | 600/443 |
| 2004/0002653 A1 | * | 1/2004 | Greppi et al. ................. | 600/439 |
| 2009/0012401 A1 | * | 1/2009 | Steinbacher .................. | 600/459 |
| 2009/0256838 A1 | * | 10/2009 | De Bliek et al. .............. | 345/419 |

FOREIGN PATENT DOCUMENTS

| | | | |
|---|---|---|---|
| JP | 04-218143 A | | 8/1992 |
| JP | 10-511590 A | | 11/1998 |
| JP | 2005143733 | * | 5/2005 |
| JP | 2005-143733 | | 6/2005 |
| JP | 2005-296156 | | 10/2005 |
| JP | 2007-102768 | | 4/2007 |
| JP | 2007-296333 | | 11/2007 |
| WO | 2005/006987 A | | 1/2005 |

OTHER PUBLICATIONS

Email_Authorization_ExaminersAmendment_051513; dated May 15, 2013.*

(Continued)

*Primary Examiner* — Kee M Tung
*Assistant Examiner* — Sing-Wai Wu
(74) *Attorney, Agent, or Firm* — Oblon, Spivak, McClelland, Maier & Neustadt, L.L.P.

(57) ABSTRACT

A transmitter/receiver transmits and receives ultrasonic waves to and from a desired region of a subject via an ultrasonic probe. A signal processor obtains a plurality of physical quantities from signals outputted by the transmitter/receiver having received ultrasonic echoes from the subject. A voxel-value generator generates a voxel value containing the plurality of physical quantities. An image generator generates a three-dimensional image by using the plurality of physical quantities including any of the rate, power value or dispersion of a blood flow contained in the voxel value and sequentially executing a rendering process on each voxel. A display controller controls a display to display the generated three-dimensional image.

16 Claims, 7 Drawing Sheets

(56) References Cited

OTHER PUBLICATIONS

ProposedAmendment_329085us_ex_am; dated May 15, 2013.*
JP2005_296156_EngXlate.*
U.S. Appl. No. 13/074,021, filed Mar. 29, 2011, Yoshida, et al.
Office Action issued Mar. 13, 2012, in Japanese Patent Application No. 2007-179788.
Office Action issued Feb. 19, 2013, in Japanese Patent Application No. 2007-179788.

* cited by examiner

ULTRASONIC IMAGING APPARATUS

BACKGROUND OF THE INVENTION

1. Field of the Invention

The present invention relates to an ultrasonic imaging apparatus configured to transmit and receive ultrasonic waves to and from a living body to obtain medical image data and display a three-dimensional image, and more specifically, relates to an ultrasonic imaging apparatus configured to display a three-dimensional color Doppler image of blood-flow information.

2. Description of the Related Art

In medical image diagnosis using an ultrasonic imaging apparatus, an X-ray CT apparatus, an MRI apparatus etc., in accordance with increase of the speed and performance of the detecting function and arithmetic process of biological information, it has become possible to perform real-time display of displaying an image almost simultaneously with acquisition of image data from a subject.

In each of the image diagnosis apparatuses described above, a plurality of different physical quantities indicating the biological characteristics of the subject are detected and imaged. An ultrasonic imaging apparatus has a plurality of capturing modes, such as the B-mode method of imaging tissue structures within a living body by using the magnitude of reflected waves of ultrasonic waves having been transmitted to the subject (hereinafter referred to as "ultrasonic echoes"), and the color Doppler method of imaging a blood flow or an organ movement velocity by using the ultrasonic Doppler effect.

Information obtained from the ultrasonic echoes in this color Doppler method is blood-flow-velocity information (its sign varies between the case of getting away from the ultrasonic probe and the case of coming close to the ultrasonic probe), power information in which velocity is differentiated (power information indicates the volume of a blood flow per unit time), and dispersion information in which variations in velocity is presented as an index.

The color Doppler method includes an image display mode such as a velocity and dispersion display mode of displaying velocity information and dispersion information of a blood flow, and a power display mode of displaying power information. This makes it possible to simultaneously display the velocity information, power information, dispersion information of a blood flow, etc. by displaying blood-flow information converted into a color map, in an ultrasonic imaging apparatus generating a two-dimensional image. For example, by using two physical quantities as parameters, arranging the parameters on the vertical axis and the horizontal axis of a two-dimensional map, respectively, and creating a color map corresponding to respective values thereof, a doctor and a laboratory technician (hereinafter referred to as an "operator") can identify the conditions of the two change quantities with colors.

Further, in recent years, as an ultrasonic imaging apparatuses, a system capable of high-speed collection and display of three-dimensional images has been rapidly developed. Thus, it has become possible to provide a diagnostic image beyond a conventional visual field, such as a three-dimensional image and a moving image of a three-dimensional image.

Furthermore, a three-dimensional ultrasonic imaging apparatus has become capable of not only forming a three-dimensional image of a living-body histological image (i.e., an image produced by the B-mode method) but also displaying a three-dimensional image by combining a three-dimensional image of an image produced by the color Doppler method (a color Doppler image) and a histological image. In this regard, in generation of a three-dimensional image, it is common to generate a three-dimensional image of a histological image, and it is uncommon to generate images of other physical parameters. However, since a color Doppler image provides a visualized image of information on a blood flow in a body, it is possible to display three-dimensional information on a blood flow by displaying as a three-dimensional image, which is becoming important display.

In the generation of a three-dimensional image, volume rendering is used. This volume rendering is as described below. For example, slice images obtained by an ultrasonic imaging apparatus are stacked. Next, a volume model having a three-dimensional structure (a voxel space) is created in which the value of each of the plurality of slice images is put into a square called a voxel. After the angle of view is determined for this volume model, voxel tracking is executed from an arbitrary viewpoint, and transmitted light and reflected light are obtained based on the opacity corresponding to the voxel value, whereby brightness is obtained. Moreover, image information based on this brightness is projected on pixels of a projection plane, and organs are sterically extracted, whereby a three-dimensional image is obtained.

Here, in the ultrasonic imaging apparatus generating and displaying a three-dimensional color Doppler image, it is preferred to three-dimensionally display the aforementioned parameters including the velocity information, power information and dispersion information of a blood flow. In this regard, as in the case of a two-dimensional image, it is possible to create a 3D color map in which colors corresponding to the three parameters are set, respectively. However, for a reason such that the human cognitive ability does not correspond, it is necessary to use a color map corresponding to two parameters in the case of displaying the values of the parameters in colors.

In general, in the case of displaying a three-dimensional image, it is necessary to project and display on a two-dimensional projection plane so that a human can easily perceive three-dimensionally arranged values. That is, the greatest difference between display of a three-dimensional image and display of a two-dimensional image is that depth information must be visualized. Moreover, in the case of a three-dimensional medical image, it is often necessary to visualize three-dimensional image data of not only the surface but also the inside.

In this regard, in three-dimensional imaging of tissue information, data equivalent to a 2D luminance signal is allocated to voxel data. Then, it is possible not to display a portion with luminance lower than a certain value by setting a threshold and transparency in accordance with the luminance, and it is possible to three-dimensionally depict a tissue with high luminance by setting higher level of luminance to be more opaque. In the case of applying this to the color Doppler method, for example, it is possible to set transparency in accordance with the velocity value, and it is possible to three-dimensionally image only a high-velocity blood flow. However, in the case of a two-dimensional color Doppler image, as described above, two parameters (e.g., the velocity value and dispersion value, or the velocity value and power value) may be simultaneously displayed in color. In this case, it is difficult to convert a 2D display image into a three-dimensional image as it is.

Thus, a technique has been proposed conventionally in which setting of opacity and setting of color tone are performed based on values of different parameters when a three-dimensional image is generated based on ultrasonic echoes obtained from a subject body by the color Doppler method (for example, refer to Japanese Unexamined Patent Application Publication JP-A 2005-143733.)

However, the conventional ultrasonic apparatus gives one physical quantity as a parameter into one voxel data and generates a three-dimensional image based thereon. Then, the apparatus performs an operation of stacking three-dimensional images generated with different parameters. Therefore, in the conventional ultrasonic apparatus, calculation for generating a three-dimensional image is complicated and processing is heavy, and moreover, effective use of the respective parameters is difficult.

In addition, in a case where a parameter indicating one physical quantity is assigned to each of the opacity setting and the color tone setting as in JP-A 2005-143733, each of the physical quantities is handled separately.

Therefore, it is impossible to use a part of allowing the operator to easily recognize the state of the subject by associating the two parameters and displaying the values in one color. Accordingly, it is difficult to reflect the relationship between the two parameters. In addition, it is difficult to display only a part conforming to the condition of the values of the two parameters.

Therefore, it is difficult to effectively display a three-dimensional image.

SUMMARY OF THE INVENTION

An object of the present invention is to provide an ultrasonic imaging apparatus in which one voxel value has a plurality of parameter values.

Further, another object of the present invention is to provide an ultrasonic imaging apparatus configured to be capable of easily performing setting of color tone and setting of opacity based on two parameters among parameters indicating a plurality of physical quantities in one voxel, and display a three-dimensional image according to the display settings.

In a first aspect of the present invention, an ultrasonic imaging apparatus comprises function parts described below. A transmitter/receiver transmits and receives ultrasonic waves to and from a desired region of a subject via an ultrasonic probe. A signal processor obtains a plurality of physical quantities from signals outputted by the transmitter/receiver having received ultrasonic echoes from the subject. A voxel-value generator generates a voxel value containing the plurality of physical quantities. An image generator generates a three-dimensional image by using the plurality of physical quantities including any of velocity, power value or dispersion of a blood flow contained in the voxel value and sequentially executes a rendering process on each voxel. A display controller controls a display to display a generated three-dimensional image.

According to the first aspect, it is possible to generate a single three-dimensional image by using a plurality of physical quantities three-contained in a voxel value. Consequently, it is possible to easily generate a three-dimensional image using a plurality of physical quantities. In addition, it is possible to present a plurality of physical quantities used for diagnosis by an operator so as to be easy to perceive on a single three-dimensional image. Accordingly, the ultrasonic imaging apparatus according to the present invention can contribute to effective diagnoses by doctors, etc.

DETAILED DESCRIPTION OF THE EMBODIMENTS

[First Embodiment]

Figure 1:
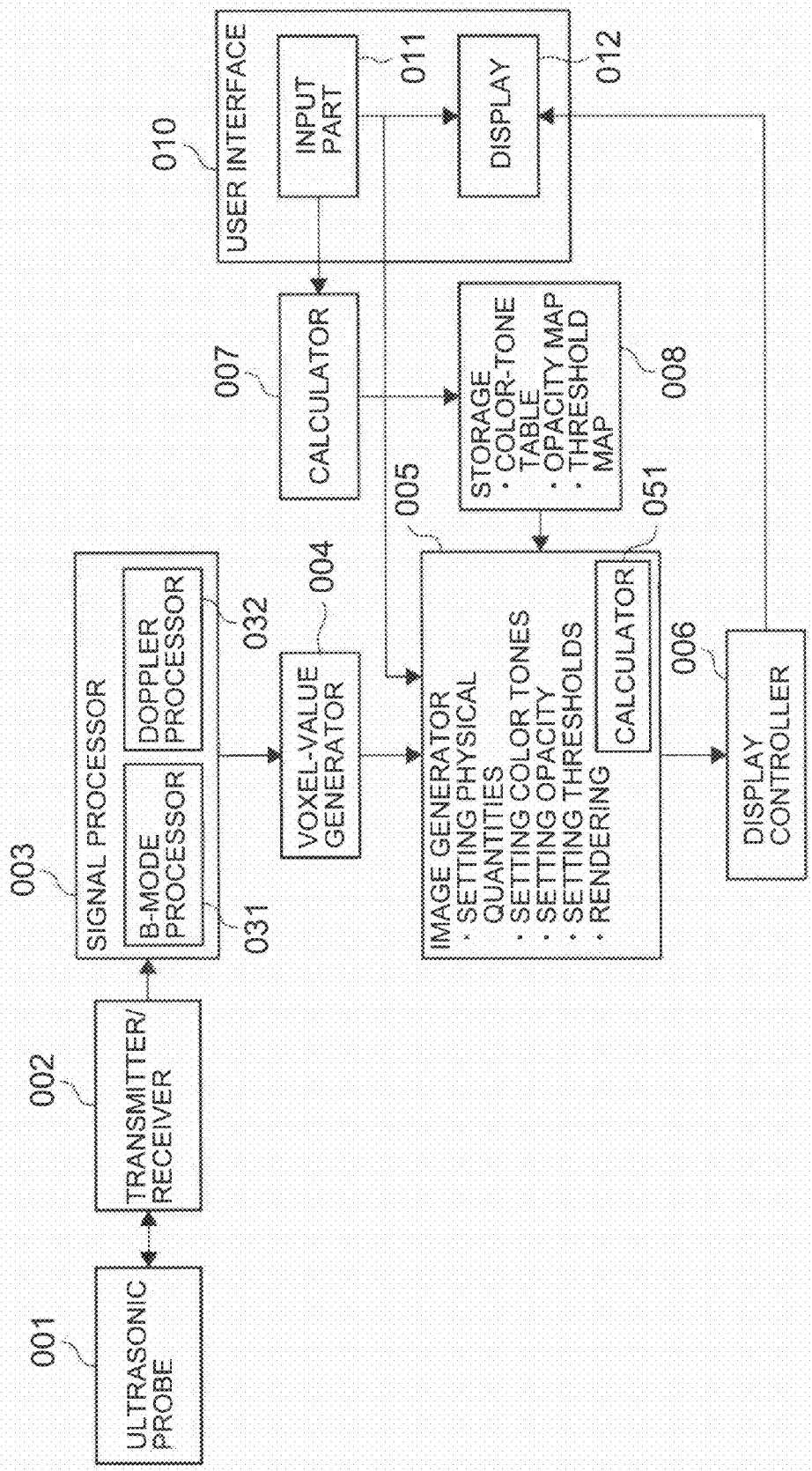
FIG. 1 is a block diagram of an ultrasonic imaging apparatus according to the present invention.

An ultrasonic imaging apparatus according to a first embodiment of the present invention will now be described. FIG. 1 is a block diagram showing the function of the ultrasonic imaging apparatus according to the present invention.

A transmitter/receiver 002 transmits ultrasonic waves to a subject via an ultrasonic probe 001. Moreover, the transmitter/receiver 002 receives the ultrasonic waves reflected from the subject (hereinafter referred to as "ultrasonic echoes") via the ultrasonic probe 001 and converts into electrical signal. Then, the transmitter/receiver 002 outputs the electrical signal obtained by the conversion to a signal processor 003. In this embodiment, the transmitter/receiver 002 described below is used when scan for B-mode images and scan for color Doppler images are performed. The transmitter/receiver 002 collects signals for B-mode images (B-mode signals) and signals for color Doppler images (color Doppler signals) in a preset three-dimensional region while repeating scan for B-mode images and scan for color Doppler images in a fixed sequence.

The signal processor 003 has a B-mode processor 031 and a Doppler processor 032. The B-mode processor 031 images amplitude information of the echoes and generates a B-mode image signal from an echo signal.

Specifically, the B-mode processor 031 executes a band-pass filter process on signals sent from the transmitter/receiver 002, detects the envelope of the outputted signal, and executes a compression process by logarithmic transformation on the detected data.

The Doppler processor 032 generates the velocity information, power information and dispersion information of a blood flow by the pulse Doppler method (PW Doppler method) or the continuous-wave Doppler method (CW Doppler method). For example, in the case of employing the pulse Doppler method, it is possible to detect Doppler shift frequency components of a certain depth by using the wave pulse. With distance resolution, it becomes possible to measure the velocity of a tissue and a blood flow in a specific site.

The Doppler processor 032 extracts the Doppler shift frequency components by phase detection of the received signal in a blood-flow observation point having a predetermined size on signals sent from the transmitter/receiver 002. Then, the Doppler processor 032 executes an FFT process on the Doppler shift frequency components to generate a Doppler frequency distribution showing the velocity information, power information and dispersion information of the blood flow in the blood-flow observation point.

In the continuous-wave Doppler method, unlike in the pulse Doppler method, not only major Doppler shift frequency components obtained in the blood-flow observation point but also all the Doppler shift frequency components in the transmitting/receiving directions of the ultrasonic waves are superimposed. The continuous-wave Doppler method is superior to the pulse Doppler method in high-speed measurement of a blood flow. The Doppler processor 032 extracts the Doppler shift frequency components by phase detection of the received signal on a sample line, which is a line for transmitting and receiving ultrasonic waves from the blood-flow observation position, on signals sent from the transmitter/receiver 002. Then, the Doppler processor 032 executes the FFT process on the Doppler shift frequency components to generate Doppler frequency components showing the velocity information, power information and dispersion information of the blood blow on the sample line.

The signal processor 003 inputs the generated B-mode image signal, and the velocity information, power information and dispersion information of the blood flow, into a voxel-value generator 004.

The voxel-value generator 004 receives the B-mode image signal, and the velocity information, power information and dispersion information of the blood flow, from the signal processor 003. In order to generate a color Doppler image, the voxel-value generator 004 obtains voxel values for color Doppler images including three physical quantities of the velocity information, power information and dispersion information, corresponding to a voxel, which is a square assigned to a three-dimensional coordinate position for transformation into the coordinate in a three-dimensional region of the subject by, for example, executing interpolation on the velocity information, power information and dispersion information near the voxel. This voxel value includes the three physical quantities of the velocity information, power information and dispersion information as parameters, and the values of those parameters become the voxel value. This voxel value is represented in the form of a matrix containing the three parameters, such as (v, p, T). Here, v denotes the value of the velocity information, p denotes the value of the power information, and T denotes the value of the dispersion information.

The data of this voxel value is stored, for example, by using 6 bits for each parameter value if the voxel value is data of 18 bits in total.

In addition, in order to generate a B-mode image, the voxel-value generator 004 obtains a voxel value for B-mode image corresponding to each voxel by, for example, executing interpolation on a B-mode image signal near the voxel received from the signal processor 003.

Next, the voxel-value generator 004 inputs the voxel values for color Doppler images and the voxel values for B-mode images corresponding to the respective voxels having been obtained, into an image generator 005.

The image generator 005 is composed of a CPU and a storage region such as a memory. The storage region of the image generator 005 stores a color-tone table in which one of the three parameters of the velocity information, power information and the dispersion information of the blood flow is taken on one axis of a two-dimensional coordinates, one of the remaining two parameters is taken on the other axis, and colors corresponding to the respective points on the two-dimensional coordinates are set.

Figure 2:
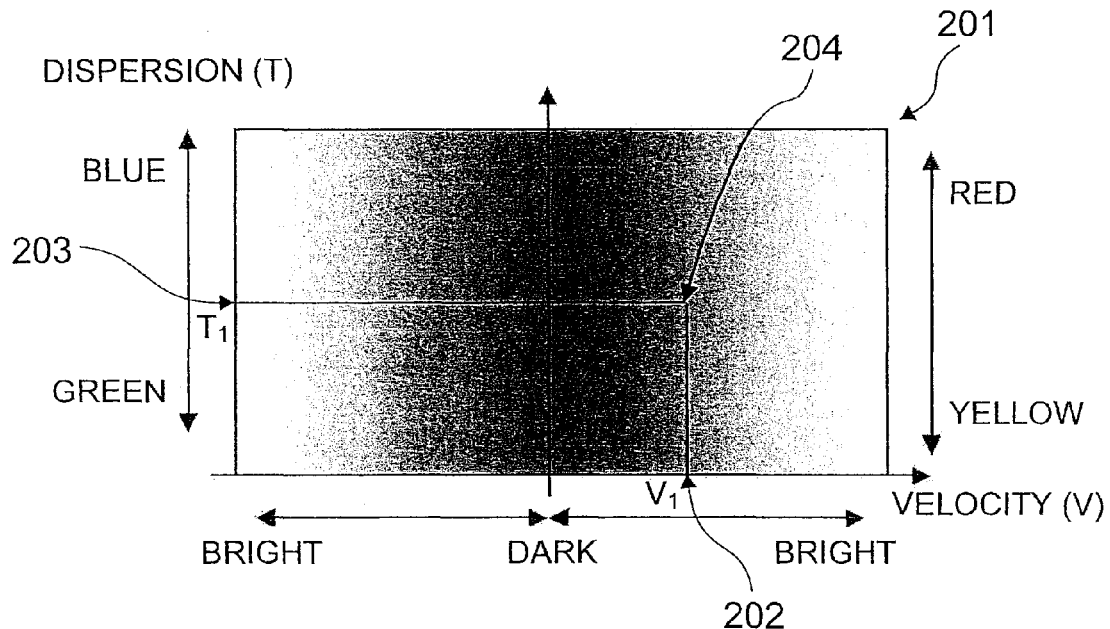
FIG. 2 is a view showing an example of a color-tone table.

Specifically, the color tone in each color-tone table is set so that the color changes from green to yellow as the value of the dispersion information becomes large, the color changes from bright red to dark red as the value of the velocity information becomes large, and the color changes from bright blue to dark blue as the value of the power information becomes large. An example of the color-tone table for velocity information and dispersion information is a color-tone table 201 shown in FIG. 2. FIG. 2 is a view showing an example of the color-tone table for velocity information and dispersion information. The color-tone table 201 in FIG. 2 is a color-tone table in which the velocity information is taken on the horizontal axis and the dispersion information is taken on the vertical axis. In the description, the color-tone table 201 of FIG. 2 is shown in monochrome, but it is actually colored with colors described beside the view.

The image generator 005 receives voxel values for B-mode images from the voxel-value generator 004 to perform a three-dimensional rendering operation ("rendering process" in the present invention) based on that voxel value. The three-dimensional rendering operation is a process of calculating luminance for displaying a three-dimensional image from the received voxel value (i.e., the original image data) on a display 012 based on the viewpoint angle, the light source, etc., or calculating the degree of display as projection data on the screen from the transparency in the three-dimensional space to create display image data. Because the data for each B-mode image is single data, it is possible to set the opacity according to signal intensity by setting the opacity (transparency) on a histogram representing the distribution of intensity of the data for B-mode images. Since the data for B-mode images indicates the state of a tissue of a subject, it is possible to set the three-dimensional depth and luminance (intensity) of a tissue desired to show on the screen by setting the opacity in the data for B-mode images.

In addition, the image generator 005 receives voxel values for color Doppler images from the voxel-value generator 004 to perform a three-dimensional rendering operation. The following description describes a case in which the operator inputs so as to set a velocity signal and a dispersion signal as parameters to display three-dimensionally. Here, the operator can select a parameter to display three-dimensionally by using a setting screen 300 for setting the opacity and threshold as shown in FIG. 3.

Figure 3:
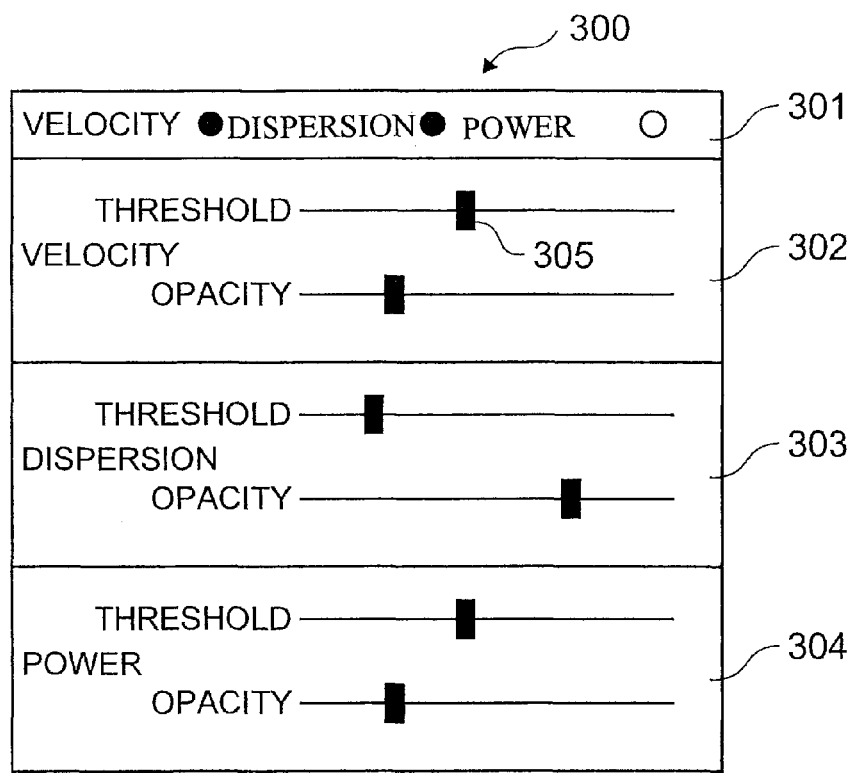
FIG. 3 is a view showing an example of a setting screen for setting the opacity and threshold.

FIG. 3 is an example of a setting screen for setting the opacity and threshold included in a user interface 010. The setting screen 300 is a screen displayed on a display 012 of the user interface 010. The user interface 010 includes an input part 011 and the display 012, and the operator uses the input part 011 to input while referring to the display 012. Then, as shown in FIG. 3, the setting screen 300 has a parameter selector 301 for selecting a parameter to three-dimensionally display, a velocity setting part 302 that sets the threshold and opacity for each parameter, a dispersion setting part 303, and a power setting part 304. Here, the threshold represents the range to display for each parameter, and a voxel having a value of a parameter equal to or more than the threshold as a voxel value is displayed on the display 012. The operator selects a parameter to three-dimensionally display from the parameter selector 301 by using the input part 011. Further, for setting the threshold and opacity of a parameter, for example, the operator moves a cursor 305 in the velocity setting part 302 by using the input part 011. At this moment, the operator moves the cursor 305 in a large-and-small range, thereby designating the position of the cursor 305. Then, a threshold corresponding to the position designated with the cursor 305 is set as the threshold of velocity. This setting method is similar to those for setting the opacity of velocity, the threshold and opacity of dispersion, and the threshold and opacity of power.

The image generator 005 receives an input by the operator, and extracts velocity signals and dispersion signals as targets to three-dimensionally display from among the voxel values. Specifically, the image generator 005 converts a voxel value (v, p, T) inputted from the voxel-value generator 004 into a voxel value (v, T).

Moreover, the image generator 005 receives an input by the operator of the threshold of values and opacity of velocity information as well as the threshold of values and opacity of dispersion information and obtains a map table of the thresholds and opacity. Here, the map table is a map that represents opacity corresponding to a color tone obtained from the combination of parameter values contained in a voxel value. That is, one opacity is obtained for one color tone from the map table.

Here, the map table of the opacity is an "opacity map" of the present invention, and the map table of the threshold is a "threshold map." The map table of the opacity and the map table of the threshold may be presented as a single map table in which opacity and threshold are combined, such as a table in which opacity is set and displayed for a voxel having a voxel value equal to or more than a certain value (velocity and dispersion in this embodiment).

In this embodiment, with a single map table in which threshold and opacity are combined, threshold and opacity are assigned to a corresponding voxel. This map table is, for example, a map table 401 shown in FIG. 4.

Figure 4:
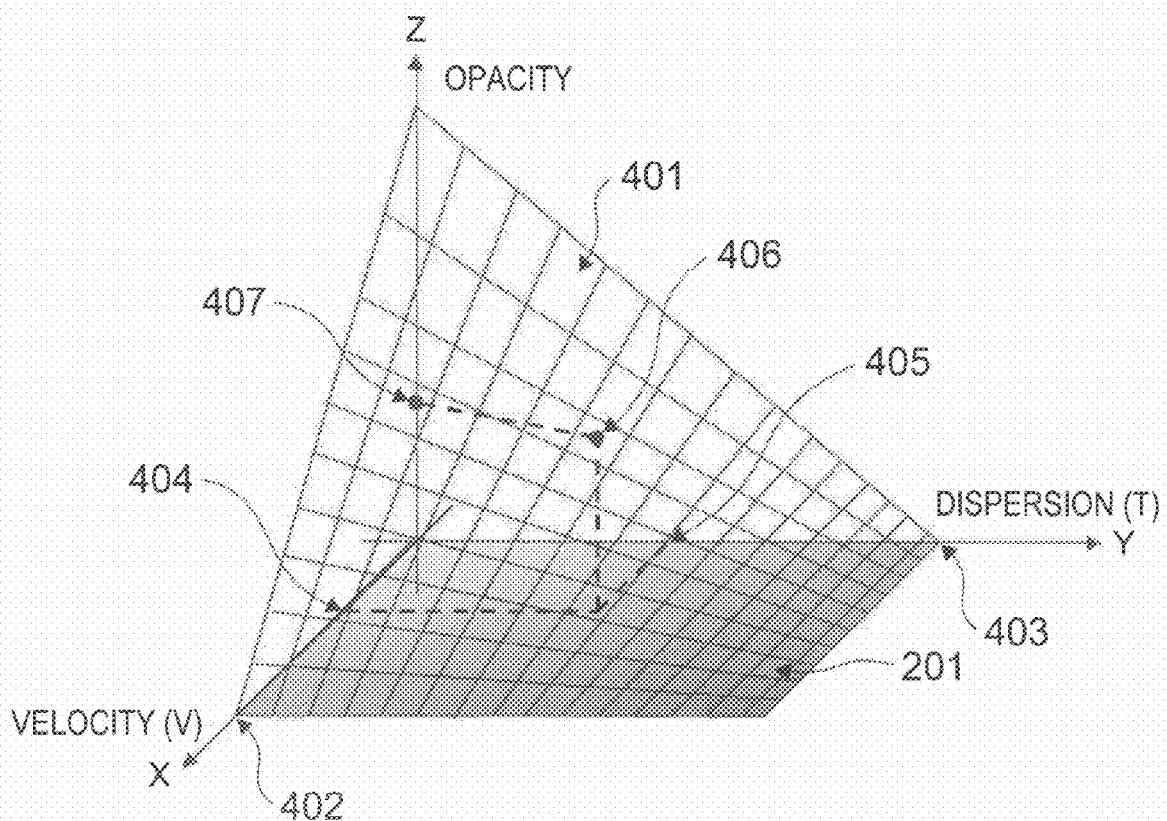
FIG. 4 is a schematic view of a map table.

FIG. 4 is a schematic view of the map table for the thresholds and opacity. A graph in FIG. 4 is a graph in which velocity information is taken on the X-axis, dispersion information is taken on the Y-axis, and opacity is taken on the Z-axis. A maximum X (velocity) value 402 and a maximum Y (dispersion) value 403 where the table and an XY plane contact become thresholds. In other words, it can be said that when the value of the opacity is minus, it exceeds the threshold. This color-tone table 201 on the X-Y coordinates of this graph in FIG. 4 is the same as the color-tone table 201 shown in FIG. 2.

A method for creating the map table 401 will now be specifically described. For example, assuming the voxel opacity is H, the velocity value is v, the dispersion value is T, the opacity of velocity (velocity emphasis coefficient) is Av, the opacity of dispersion (dispersion emphasis coefficient) is At, the threshold of velocity is hv, the threshold of dispersion is ht, and the weighting of velocity for dispersion (velocity emphasis rate) is α, the opacity is expressed by Formula 1.

$$H = \alpha \times Av \times (V-hv)2 \times (1-\alpha) \times At \times (T-ht)2 + \alpha \times (Av/5) \times (V-hv) + (1-\alpha) \times (At/5) \times (T-ht) \qquad \text{Formula 1}$$

In a case where
X=(v−hv) and
Y=(T−ht),
X=0 when X<0, and
Y=0 when Y<0,
whereby the map table 401 is created.

This Formula 1 is equivalent a "formula for obtaining the opacity from a plurality of parameters," and designation of ranges of X and Y are equivalent to designation of "the thresholds of the plurality of parameters for specifying a range of displaying the three-dimensional image."

Figure 7:
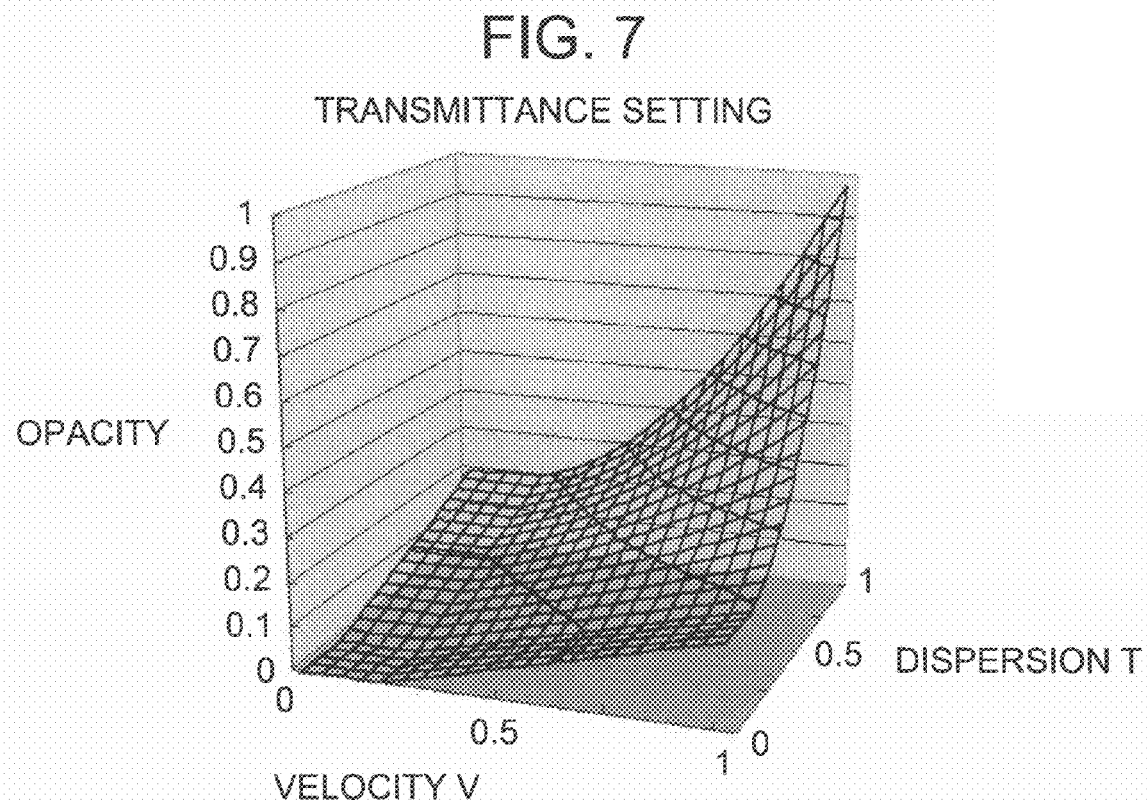
FIG. 7 is a view of an example of a map table generated by using Formula 1.
Figure 8:
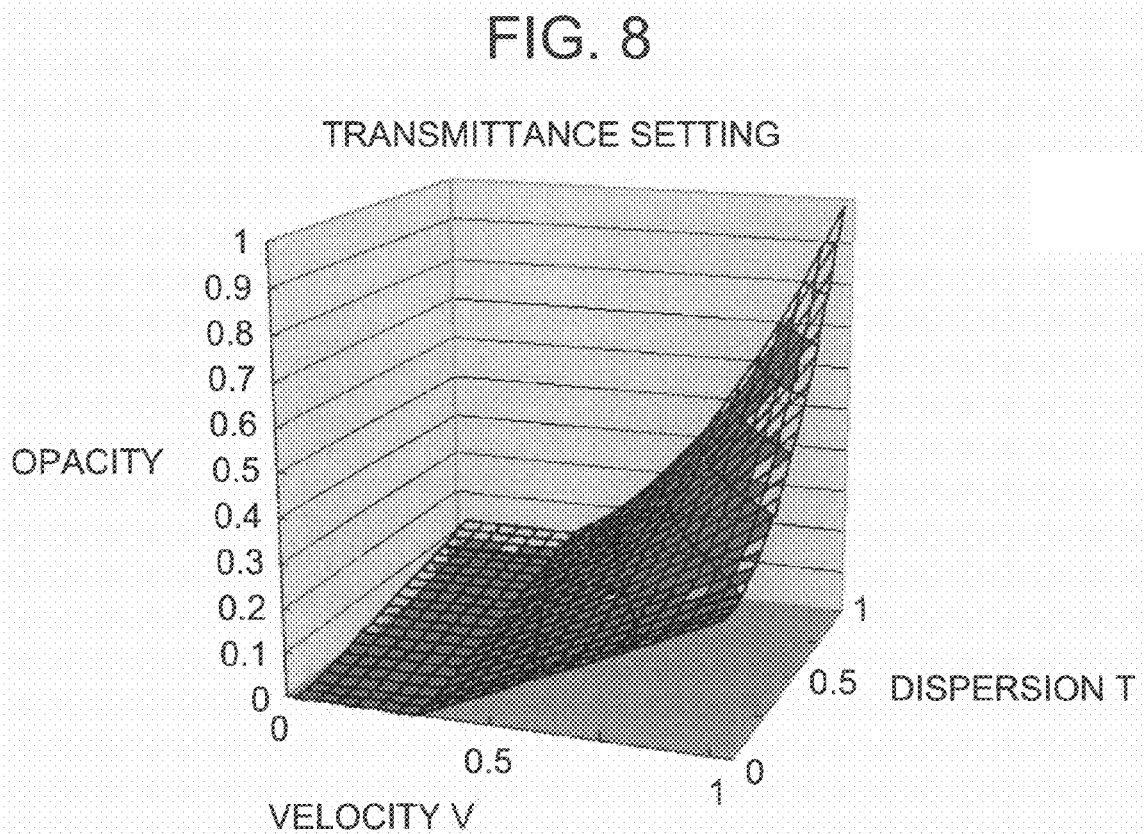
FIG. 8 is a view of an example of a map table generated by using Formula 1.
Figure 9:
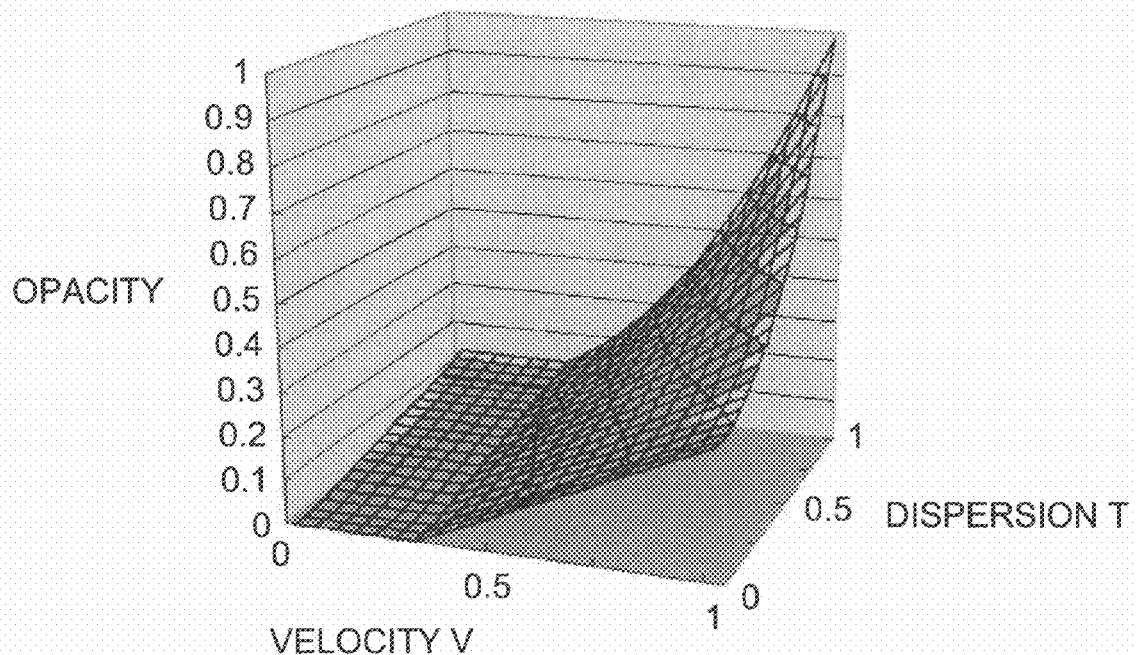
FIG. 9 is a view of an example of a map table generated by using Formula 1.

Examples of the map table 401 created by the method described above are map tables shown in FIG. 7, FIG. 8 and FIG. 9. Here, each of FIGS. 7, 8 and 9 is a view of an example of the map table in which the thresholds of velocity and dispersion and opacity are changed. The map table 401 that represents opacity corresponding to the color-tone table 201 is the "opacity map" and the "threshold map" of the present invention. Each of FIGS. 7 to 9 is a graph in which velocity is taken on the X-axis, dispersion is taken on the Y-axis and opacity is taken on the Z-axis. The opacity is a value represented by a ratio in which 0 is white and 1 is black.

FIG. 7 shows a map table in a case where each parameter is set as shown in Table 1.

TABLE 1

| α: velocity emphasis rate | 0.5 |
| Av: velocity emphasis coefficient | 2.4 |
| At: dispersion emphasis coefficient | 2.4 |
| hv: threshold of velocity | 0.2 |
| ht: threshold of dispersion | 0.2 |

FIG. 8 shows a map table in a case where each parameter is set as shown in Table 2.

TABLE 2

| α: velocity emphasis rate | 0.5 |
| Av: velocity emphasis coefficient | 3.5 |
| At: dispersion emphasis coefficient | 1.7 |
| hv: threshold of velocity | 0.3 |
| ht: threshold of dispersion | 0.1 |

FIG. 9 shows a map table in a case where each parameter is set as in Table 3.

TABLE 3

| α: velocity emphasis rate | 0.5 |
| Av: velocity emphasis coefficient | 5.8 |
| At: dispersion emphasis coefficient | 5.7 |
| hv: threshold of velocity | 0 |
| ht: threshold of dispersion | 0 |

Moreover, as other examples of the map table 401, assuming the voxel opacity is H, the velocity value is v, the dispersion value is T, the opacity of velocity (velocity emphasis coefficient) is Av, the opacity of dispersion (dispersion emphasis coefficient) is At, the threshold of velocity is hv, the threshold of dispersion is ht, and the weighting of velocity for dispersion (velocity emphasis rate) is α, the opacity can be expressed by Formula 2.

$$H = \alpha \times Av \times (V-hv)2 + (1-\alpha) \times At \times (T-ht)2 \qquad \text{Formula 2}$$

In a case where
X=(v−hv) and
Y=(T−ht),
X=0 when X<0 and
Y=0 when Y<0,
whereby the map table 401 is created.

This Formula 2 is equivalent to the "formula for obtaining the opacity from a plurality of parameters," and designation of ranges of X and Y is equivalent to the "thresholds of the plurality of parameters for specifying a range to display the three-dimensional image."

Figure 10:
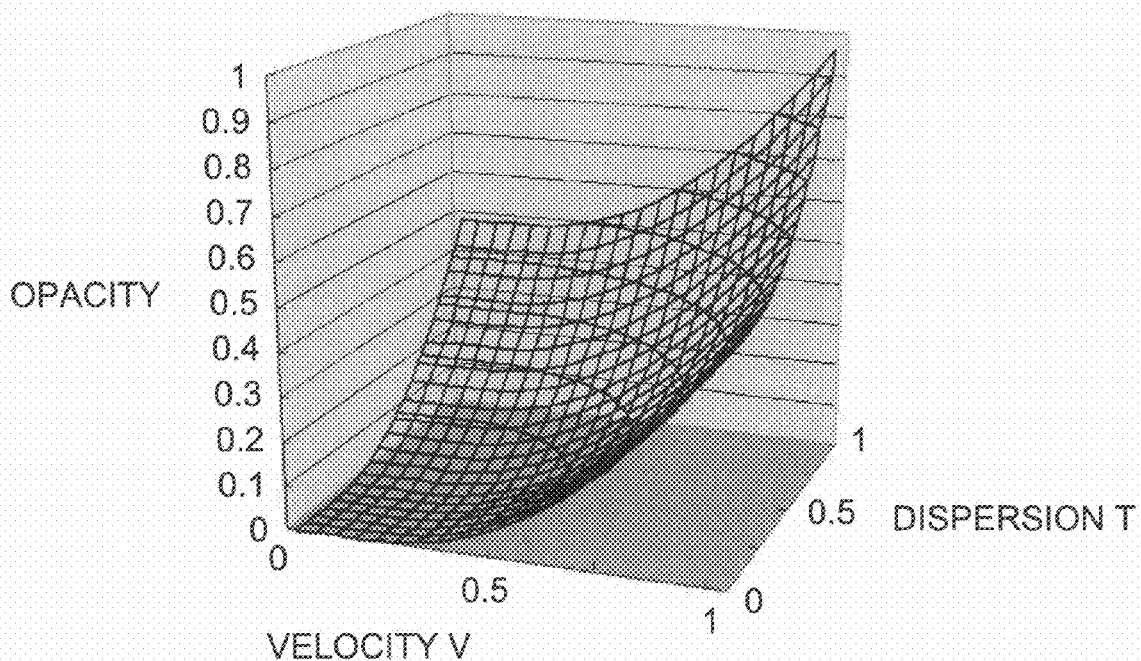
FIG. 10 is a view of an example of a map table generated by using Formula 2.
Figure 11:
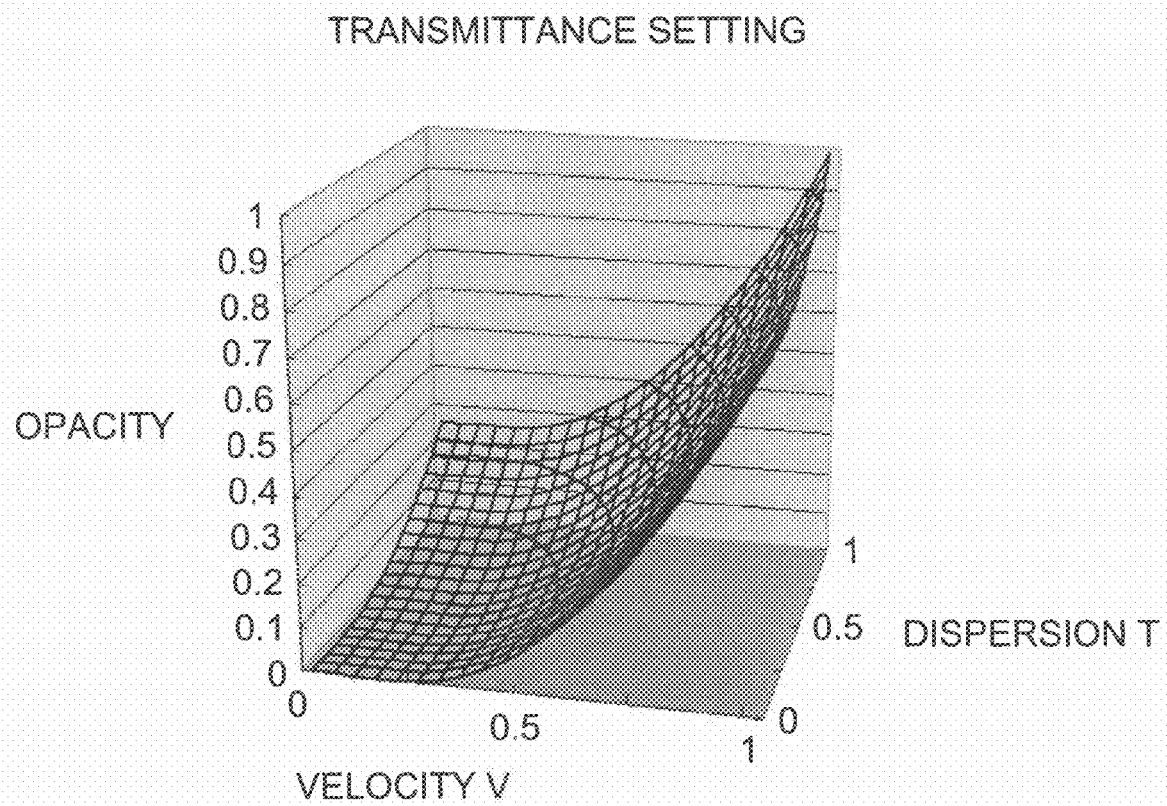
FIG. 11 is a view of an example of a map table generated by using Formula 2.

Examples of the map table 401 created with the method described above include the map tables shown in FIG. 10 and FIG. 11. Here, FIG. 10 and FIG. 11 are each views of example map tables in which the thresholds of velocity and dispersion and opacity are changed. The map table 401 that represents opacity corresponding to this color-tone table 201 is an "opacity map" and a "threshold map" of the present invention." Both FIG. 10 and FIG. 11 are graphs in which the X-axis represents velocity, the Y-axis represents dispersion, and the Z-axis represents opacity. The opacity is a value represented by a ratio in which 0 is white and 1 is black.

FIG. 10 shows a map generated when each parameter is set as shown in Table 4.

TABLE 4

| α: velocity emphasis rate | 0.5 |
| Av: velocity emphasis coefficient | 1.5 |
| At: dispersion emphasis coefficient | 1.5 |
| hv: threshold of velocity | 0.2 |
| ht: threshold of dispersion | 0.2 |

FIG. 11 shows a map generated when each parameter is set as shown in Table 5.

TABLE 5

| α: velocity emphasis rate | 0.6 |
| Av: velocity emphasis coefficient | 1.9 |
| At: dispersion emphasis coefficient | 1 |
| hv: threshold of velocity | 0.2 |
| ht: threshold of dispersion | 0.2 |

In this way, based on the thresholds and opacity for a plurality of parameters inputted by the operator, a map table of opacity and threshold satisfying the requirements is created, so that it becomes possible to easily form a map table with the desired opacity and threshold for each color tone in the color-tone table.

Next, the image generator 005 first sets the velocity information value in each voxel to 6 bits and the dispersion information value to 6 bits. As the color tone of the voxel, with reference to the color-tone table 201 as shown by the X- and Y-axes of the graph in FIG. 4 (i.e., a color-tone table similar to the color-tone table 201 in FIG. 2), a specified value is assigned to the voxel from the combination of the velocity information value and the dispersion information value. Specifically, for example, in a case where the voxel value is (v, T)=($v_1$, $T_1$), assuming a point 202 in FIG. 2 represents velocity $v_1$ and a point 203 represents dispersion $T_1$, the color tone represented at a point 204 is assigned as the color tone for the voxel value ($v_1$, $T_1$).

Moreover, the image generator 005 obtains values for calculating the opacity and threshold from the voxel values and, with reference to the map table 302, obtains the opacity corresponding to the assigned color tone.

Figure 5:
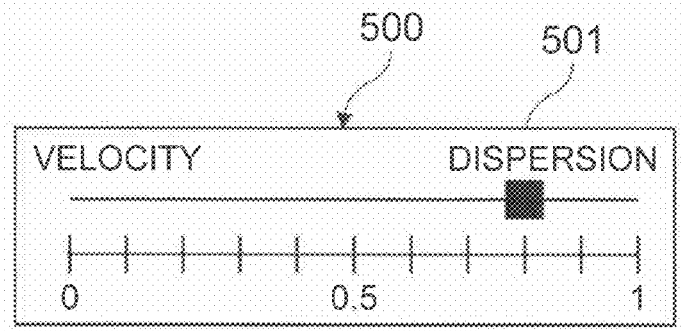
FIG. 5 is a view showing an example of a setting screen for setting the weighting of the opacity.

Specifically, the image generator 005 first receives an input of the ratio of the weighting of each parameter by the operator using the user interface 010 and performs weighting for the opacity and threshold for the velocity information value and the dispersion information value contained in the voxel value. This weighting is the "weighting in display" of the present invention. Consequently, it is possible to determine the ratio for which parameter (physical quantity) will be prioritized in the opacity. The ratio of velocity to dispersion is 0.8:0.2 in the following description. Here, for input of the weighting by the operator, a setting screen 500 in which the display 012 in the user interface 010 is displayed as shown in FIG. 5 is used. In this setting screen 500, a cursor 501 is placed at the position of the relevant percentage, with the whole being treated as having the value 1, and the ratio of the weighting of each parameter is determined with the ratio between the right and the left corresponding to the position of that cursor 501. FIG. 5 is a view showing an example of the setting screen for the weighting of the opacity. Here, the setting screen 500 is displayed on the display 012 included in the user interface 010. FIG. 5 shows the setting screen 500 set in such a ratio that the velocity is 0.8 and the dispersion is 0.2. For example, in a voxel value in which the velocity is 0.4 and the dispersion is 0.6, velocity=0.4×0.8=0.32 and dispersion=0.6×0.2=0.12. Then, each result is added to obtain a value (hereinafter this value is referred to as "opacity-calculation target value") for calculating the opacity. That is, (v×0.8, T×0.2)=(0.32, 0.12) becomes an opacity-calculation target value in the aforementioned voxel. Then, based on this opacity-calculation target value, the opacity is determined referring to the map table 401. Specifically, assuming a point 404 shown in FIG. 4 represents velocity 0.32 and a point 405 represents dispersion 0.12, a point with one color tone is determined on the XY plane. Then, a point 406 on the map table 401 corresponding to a point with that color tone is obtained. Then, a value in the Z direction of the point 406 (i.e., the opacity represented at a point 407) will be the opacity assigned to the opacity-calculation target value (0.32, 0.12). Here in this embodiment, in order to display an image that is easy to perceive and that meets the operator's requirements, the weighting of the opacity for each parameter is performed. However, it is also possible to set the opacity without performing this weighting.

The image generator 005 executes a three-dimensional rendering operation similar to that used for B-mode images on voxels with a value equal to or more than the threshold, by using the color tone and opacity for the voxel (i.e., using a color tone with the opacity as a voxel value), and obtains display image data.

The image generator 005 inputs the display image data for B-mode images and the display image data for color Doppler images obtained in the three-dimensional rendering operation, into a display controller 006.

The display controller 006 controls to display the display image data for B-mode images and the display image data for color Doppler images in combination with corresponding points of the two-dimensional coordinates on the display 012, thereby controlling the display 012 to display a three-dimensional image in which a B-mode three-dimensional image, which is a three-dimensional image of a histological image, and a color Doppler three-dimensional image, which is a three-dimensional image of blood flow volume, are combined.

Figure 6:
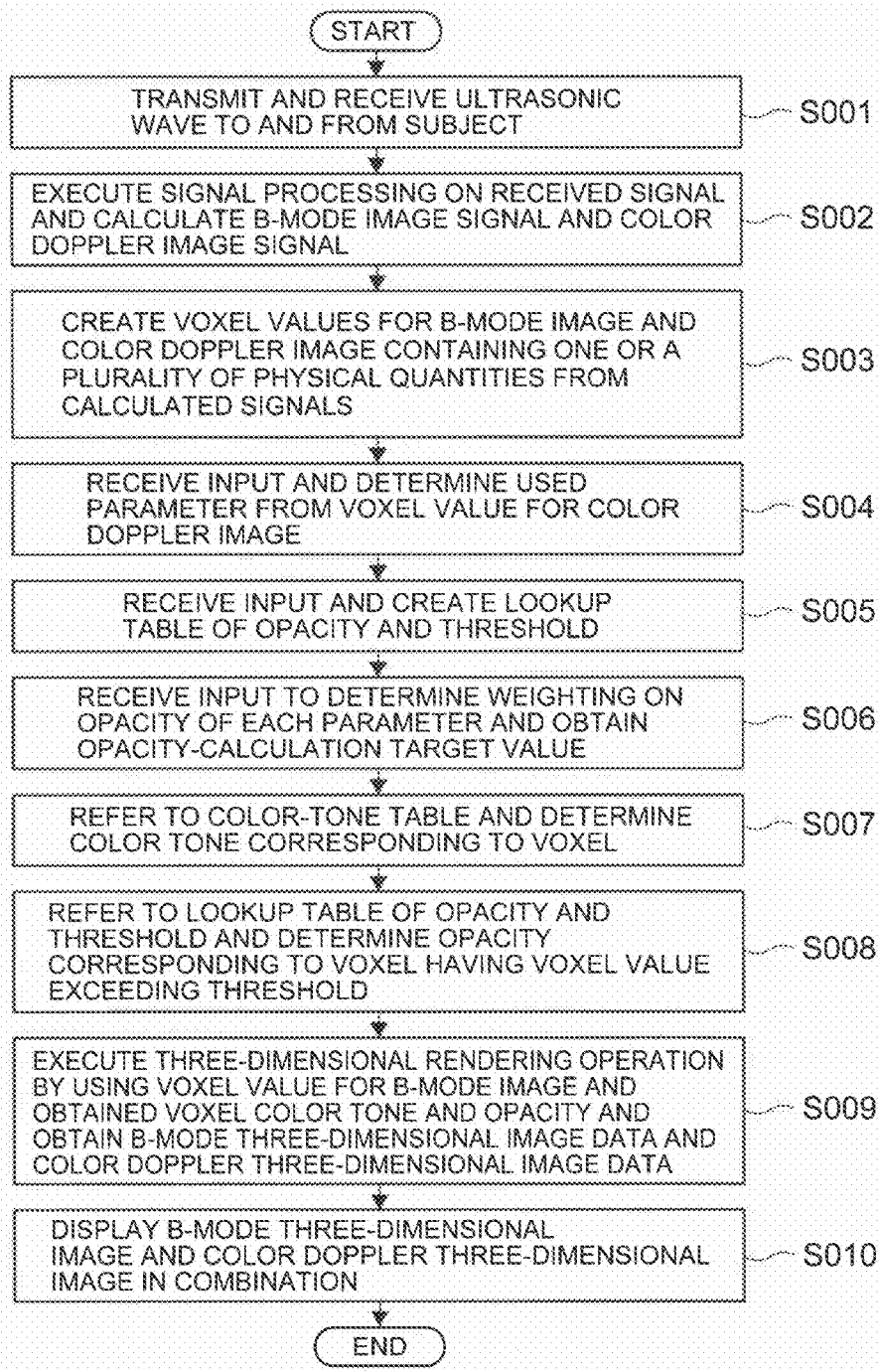
FIG. 6 is a flowchart of display of a three-dimensional image in an ultrasonic imaging apparatus according to a first embodiment.

Next, with reference to FIG. 6, the operational flow for generating images of the ultrasonic imaging apparatus according to this embodiment will now be explained. FIG. 6 is a flowchart of the operations for generating images of the ultrasonic imaging apparatus according to this embodiment.

Step S001: The transmitter/receiver 002 transmits and receives ultrasonic waves to and from a subject via the ultrasonic probe 001 and outputs received signals to the signal processor 003.

Step S002: The signal processor 003 executes signal processing on the signals inputted from the transmitter/receiver 002 and calculates B-mode image signals and color Doppler image signals. The signal processor 003 outputs the calculated B-mode image signals and color Doppler image signals to the voxel-value generator 004.

Step S003: The voxel-value generator 004 creates voxel values for B-mode images having a luminance value as values based on the B-mode image signals inputted from the signal processor 003, and also creates voxel values for color Doppler images containing a plurality of physical quantities (velocity, power and dispersion of a blood flow) based on the color Doppler image signals inputted from the signal processor 003.

Step S004: The image generator 005 receives an input by the operator through the input part 011 to select a parameter to use from the voxel values for color Doppler images. Here, velocity and dispersion are selected.

Step S005: A calculator 007 receives an input by the operator of the thresholds of velocity and dispersion and the opacity from the user interface 010 having the screen 300 (refer to FIG. 3), and calculates the map table 401 (refer to FIG. 4) of the opacity and thresholds for determining the opacity of each color tone in the color-tone table 201 corresponding to combinations of velocity and dispersion stored in the storage 008. The calculator 007 causes the storage 008 to store the map table of the opacity and thresholds having been calculated.

Step S006: The operator sets the weighting to the opacity of velocity and dispersion by using the user interface 010 having the setting screen 500 (refer to FIG. 5). Then, the image generator 005 receives the weighting to the opacity of velocity and dispersion by the operator, and executes the weighting to the opacity on a plurality of parameters contained in a voxel value having been inputted from the voxel-value generator 004 to obtain the opacity-calculation target value.

Step S007: The image generator 005 refers to the color-tone table 201 of the combination of velocity and dispersion stored in the storage 008, and obtains the color tone of each voxel based on the velocity and dispersion contained in the voxel value having been inputted from the voxel-value generator 004.

Step S008: The image generator 005 refers to the map table 401 of the opacity and threshold, and determines the opacity corresponding to each voxel whose voxel value exceeds the threshold based on the obtained opacity-calculation target value.

Step S009: The image generator 005 executes the three-dimensional rendering operation on each voxel based on the voxel value for B-mode image, and obtains B-mode three-dimensional image data. Further, the image generator 005 executes the three-dimensional rendering operation on each voxel based on the color tone and opacity of a voxel having a voxel value for color image exceeding the threshold, and obtains three-dimensional image data of color Doppler image. Furthermore, the image generator 005 outputs the B-mode three-dimensional image data and the three-dimensional image data of color Doppler image that have been obtained, to the display controller 006.

Step S010: The display controller 006 combines the B-mode three-dimensional image data and the three-dimensional image data of color Doppler image that have been inputted from the image generator 005, and controls the display 012 to display a three-dimensional image in which a B-mode three-dimensional image and a three-dimensional image of a color Doppler image are combined.

(Effect)

As described above, the ultrasonic imaging apparatus according to this embodiment makes it possible to make a plurality of physical quantities composing a blood-flow image contained in a voxel value as parameters (a velocity value and a dispersion value in this embodiment). Consequently, it is possible to simultaneously handle a plurality of parameters in one image processing, and it is possible to easily obtain the color tone of a voxel from color-tone tables including combinations of the respective parameters.

Moreover, as a method of setting the opacity (including a threshold) for a voxel, it is possible to use a user interface similar to that used in the conventional opacity setting and threshold setting. Additionally, since the user can set the weighting between velocity and dispersion by using a simple user interface, it becomes possible to easily assign set values for three-dimensional display to all color Doppler images on a two-dimensional map.

Further, the ultrasonic imaging apparatus according to this embodiment makes it possible to make two parameters (e.g., velocity and dispersion) contained in two color Doppler image voxel values.

Consequently, for example, in the case of observation of regurgitation of a blood flow in a heart, it is possible to visualize dispersion components to easily visualize disorder of the flow due to the regurgitation, whereby the operator can easily grasp a three-dimensional range thereof. Moreover, the operator can quantify the regurgitated volume by using the velocity value of the blood flow within the range.

Furthermore, this embodiment describes the ultrasonic imaging apparatus that receives a voxel value containing three physical quantities from the voxel-value generator and uses two of the three physical quantities as parameters, but it is also possible to use only one of the physical values contained in the voxel value having been received from the voxel-value generator and display a three-dimensional image. In this case, it is possible to set a color tone and opacity, and generate a three-dimensional image using them, in an operation as conventional.

In the above description, the ultrasonic imaging apparatus according to this embodiment uses two parameters, but it can also be operated in a configuration that uses two or more parameters to obtain the opacity (e.g., a configuration that uses three parameters of velocity, power value and dispersion of a blood flow to obtain the transparency).

Further, in this embodiment, a map is created based on a mathematical formula for obtaining opacity, and the opacity corresponding to a parameter is obtained from the created map, but it is also possible to configure so as to obtain the opacity to become a voxel value directly from the mathematical formula. In this case, a calculator 051 included in the image generator 005 obtains the opacity of each voxel based on the mathematical formula for obtaining the opacity from a plurality of parameters. Then, the image generator 005 executes rendering based on the obtained voxel value.

[Second Embodiment]

Next, an ultrasonic imaging apparatus according to a second embodiment of the present invention will be described. The ultrasonic imaging apparatus according to this embodiment is configured to, in the ultrasonic imaging apparatus according to the first embodiment, have a fixed lookup table showing the threshold and opacity corresponding to each color-tone table stored in the storage 008 previously. Below, the lookup table previously stored in the storage 008 and the calculation of a voxel value to become a value for three-dimensional rendering operation using the table will be described. The configuration of the ultrasonic imaging apparatus according to this embodiment is also shown by the block diagram of FIG. 1, similarly to the ultrasonic imaging apparatus according to the first embodiment.

The storage 008 previously stores a lookup table in which correspondence of color tone and opacity corresponding to each color-tone table (i.e., a color-tone table of velocity and dispersion, a color-tone table of dispersion and power, and a color-tone table of velocity and power) is described. This lookup table is equivalent to an "opacity map" and a "threshold map" of the present invention.

Here, in a case where the value of velocity information is set to 6 bit and the value of dispersion information is set to 6 bit in one voxel as in the first embodiment, there are 4,096 (64×64) patterns of combinations of color tones. Although a lookup table having 4,096 patterns of color tones and opacities is necessary to set the opacities corresponding to all of the color tones, it is possible to roughly grasp the condition of each parameter expressed in a three-dimensional image without making changes in transparency so precisely, and therefore, it is possible to set opacities each corresponding to a package of color tones. In addition, it is very complicated to set the correspondence of the opacity of each of the color tones. Therefore, in this embodiment, the thresholds and opacity are set for a 64-level scale. The scale of the opacity and threshold may be another scale.

The image generator 005 receives an input from the voxel-value generator 004, and first refers to the color-tone table 201 stored in the storage 008 to determine the color tone of each voxel.

Next, the image generator 005 obtains an opacity-calculation target value for each voxel by using the weighting of each parameter on the opacity having been inputted from the user interface 010 by the operator.

The image generator 005 rounds the obtained opacity-calculation target value so as to apply to the aforementioned lookup table of the opacity shown by the 64-level scale, and determines the opacity of each voxel based on the correspondence.

In this way, in the ultrasonic imaging apparatus in this embodiment, the color tone and opacity, which are voxel values for performing the three-dimensional rendering operation, are obtained.

As described above, in the ultrasonic imaging apparatus of this embodiment, it is possible to obtain the opacity of each voxel by using a previously stored lookup table that shows the correspondence of color tones and opacity. Consequently, even if the operator does not set the threshold and opacity for each parameter (physical quantity) in each time, it is possible to generate a three-dimensional image that represents two parameters.

Further, because it is always represented with the same opacity and threshold, it becomes possible to efficiently diagnose. Moreover, because the need for calculating a map table from the threshold and opacity for each parameter is eliminated, the load on the ultrasonic imaging apparatus for image processing can be reduced.

[Third Embodiment]

Next, an ultrasonic imaging apparatus according to a third embodiment of the present invention will be described. The ultrasonic imaging apparatus according to this embodiment uses two of the parameters contained in the voxel value separately to determine the color tone and set the opacity, respectively. The configuration of the ultrasonic imaging apparatus according to this embodiment is also similar to the configuration shown in the block diagram of FIG. 1.

The ultrasonic imaging apparatus according to this embodiment operates as in the first embodiment, from transmission/reception of ultrasonic waves to and from a subject by the transmitter/receiver 002 to generation of voxel values by the voxel-value generator 004. Therefore, an operation after the generation of the voxel values will be described below. Moreover, in the following description, it is assumed that the operator has set velocity as a parameter for determining a color tone and has set dispersion as a parameter for determining opacity.

The image generator 005 receives a voxel value (v, p, T) from the voxel-value generator 004. Next, the image generator 005 extracts velocity v, which is the velocity contained in the voxel value, as the parameter for determining color tone, and dispersion T as the parameter for determining opacity.

The image generator 005 refers to a previously stored color-tone table that corresponds to changes in velocity, thereby determining a color for each voxel.

Moreover, the image generator 005 receives an input of the opacity for dispersion by the operator, and determines the opacity of each voxel by using the opacity.

Furthermore, the image generator 005 performs the three-dimensional rendering operation based on the obtained color tone and opacity of each voxel to generate three-dimensional image data.

The display controller 006 controls the display 012 to display a three-dimensional image based on the three-dimensional image data received from the image generator 005.

As described above, the ultrasonic imaging apparatus according to this embodiment makes it possible to accelerate the processing by handling the respective parameters individually. In addition, because a voxel value contains a plurality of physical quantities, it is possible to easily select physical quantities as parameters, and it becomes possible to easily display three-dimensional images desired by the operator.

What is claimed is:

1. An ultrasonic imaging apparatus comprising:
a transmitter/receiver configured to transmit and receive ultrasonic waves to and from a desired region of a subject via an ultrasonic probe;
a signal processor configured to obtain a plurality of physical quantities including at least two of rate, power value, and dispersion of a blood flow, from signals outputted by the transmitter/receiver having received ultrasonic echoes from the subject for a particular voxel, the voxel being assigned to a three-dimensional coordinate position;
a voxel-value generator configured to generate a voxel value, which is arranged as a vector containing a plurality of values, corresponds to the respective voxel, and contains the plurality of physical quantities obtained by the signal processor as the values for the voxel value;
an image generator configured to sequentially execute a rendering process based on the voxel value by using the plurality of physical quantities contained in the voxel value to generate a three-dimensional image; and
a display controller configured to control a display to display the generated three-dimensional image,
wherein two physical quantities of the plurality of physical quantities are selected and a threshold and opacity are set for each of the two physical quantities, and
wherein after the threshold and the opacity are set, a weighting for the two physical quantities is set and a map-table, that corresponds to the threshold and the opacity, is created.

2. The ultrasonic imaging apparatus according to claim 1, wherein the image generator includes a calculator configured to calculate opacity for each voxel from the plurality of physical quantities, sets the opacity as a opacity value, and executes a rendering process based on the opacity value.

3. The ultrasonic imaging apparatus according to claim 1, wherein the image generator indicates the plurality of physical quantities contained in the voxel value as a plurality of parameters, receives an input from a user interface configured to change weighting of the plurality of parameters, changes the weighting of the parameters in display, and executes a rendering process based on the weighting.

4. The ultrasonic imaging apparatus according to claim 2, wherein the calculator is configured to be capable of receiving a mathematical formula for calculating opacity corresponding to a plurality of parameters from a user interface, and calculates opacity for the voxel based on the mathematical formula for calculating the opacity corresponding to the plurality of parameters having been inputted from the user interface.

5. The ultrasonic imaging apparatus according to claim 2, wherein the calculator previously stores thresholds of a plurality of parameters for specifying a range to display the three-dimensional image, calculates opacity from the voxel value contained in the range to display, and executes a process not to display the voxel out of the range to display.

6. The ultrasonic imaging apparatus according to claim 2, wherein the calculator is configured to be capable of receiving a mathematical formula for calculating opacity corresponding to a plurality of parameters from a user interface, calculates opacity from the voxel value contained in the range to display based on thresholds of the plurality of parameters for specifying a range to display the three-dimensional image having been inputted from the user interface, and executes a process not to display the voxel out of the range to display.

7. The ultrasonic imaging apparatus according to claim 1, further comprising a storage configured to store a color-tone table corresponding to values of two parameters of a plurality of parameters contained in the voxel value,
wherein the image generator refers to the color-tone table to set a color tone corresponding to the parameter value contained in the voxel value as a voxel value, and executes the rendering process based on the color tone.

8. The ultrasonic imaging apparatus according to claim 7, wherein:
the storage stores a previously created opacity map showing opacity corresponding to each color tone of the color-tone table; and
the image generator refers to the opacity map to set a color tone having the opacity corresponding to the color tone set to the voxel value as a voxel value.

9. The ultrasonic imaging apparatus according to claim 1, wherein the voxel value generated from the plurality of physical quantities is used to generate color-tone and transparency values for each voxel, and a respective number of levels of the transparency is less than a number of levels of the color tone.

10. The ultrasonic imaging apparatus according to claim 1, wherein the calculator is configured to determine a color-tone of the voxel to be displayed using two physical quantities included in the voxel value, and to determine an opacity of the voxel to be displayed using the two physical quantities used to determine the color tone, so as to determine one opacity per one color-tone from the map-table.

11. The ultrasonic imaging apparatus according to claim 1, wherein the calculator is configured to determine a color-tone of the voxel to be displayed using each of the physical quantities included in the voxel value, and to determine an opacity of the voxel to be displayed using each of the physical quantities used to determine the color tone, so as to determine one opacity per one color-tone from the map-table.

12. The ultrasonic imaging apparatus according to claim 10, wherein the map-table is a three-dimensional graphical map-table.

13. The ultrasonic imaging apparatus according to claim 11, wherein the map-table is a three-dimensional graphical map-table.

14. The ultrasonic imaging apparatus according to claim 1, wherein at least one of the threshold and opacity values on a setting screen is changed by dragging a cursor between a range from small to large.

15. The ultrasonic imaging apparatus according to claim 1, wherein the signal processor further configured to obtain a plurality of physical quantities including each of rate, power value, and dispersion of a blood flow for a particular voxel.

16. An ultrasonic imaging apparatus comprising:
a transmitter/receiver configured to transmit and receive ultrasonic waves to and from a desired region of a subject via an ultrasonic probe;
a signal processor configured to obtain a plurality of physical quantities including at least two of rate, power value, and dispersion of a blood flow, from signals outputted by the transmitter/receiver having received ultrasonic echoes from the subject for a particular voxel, the voxel being assigned to a three-dimensional coordinate position;
a voxel-value generator configured to generate a voxel value, which is arranged as a vector containing a plurality of values, corresponds to the respective voxel, and contains the plurality of physical quantities obtained by the signal processor as the values for the voxel value;
an image generator configured to sequentially execute a rendering process based on the voxel value by using the plurality of physical quantities contained in the voxel value to generate a three-dimensional image; and
a display controller configured to control a display to display the generated three-dimensional image,
wherein two physical quantities of the plurality of physical quantities are selected and a threshold and opacity are set for each of the two physical quantities,
wherein after the threshold and the opacity are set, a weighting for the two physical quantities is set and a map-table, that corresponds to the threshold and the opacity, is created, and
wherein the threshold and opacity values on a setting screen are each changed by dragging a cursor between a range from small to large.

* * * * *